United States Patent von dem Hagen et al.

[11] Patent Number: 4,972,831
[45] Date of Patent: Nov. 27, 1990

[54] GAS RATIO CONTROLLING DEVICE FOR ANESTHETIC APPLIANCES

[75] Inventors: Tronje von dem Hagen, Lübeck; Eckhard Schmudde, Pansdorf; Carl-Friedrich Wallroth, Lübeck, all of Fed. Rep. of Germany

[73] Assignee: Dragerwerk Aktiengesellschaft, Lübeck, United Kingdom

[21] Appl. No.: 321,572

[22] Filed: Mar. 9, 1989

[30] Foreign Application Priority Data

Mar. 30, 1988 [DE] Fed. Rep. of Germany ....... 3810745

[51] Int. Cl.$^5$ ................. A61M 16/01; A61M 16/12; A62B 7/01; A62B 7/10
[52] U.S. Cl. ....................... 128/204.21; 128/204.25; 128/205.24
[58] Field of Search .................. 128/203.25, 203.12, 128/203.14, 204.18, 204.21, 204.25, 205.24, 204.22

[56] References Cited

U.S. PATENT DOCUMENTS

| | | | |
|---|---|---|---|
| 3,251,361 | 5/1966 | Rusz | 128/203.25 |
| 3,669,134 | 6/1972 | Dobritz | 128/203.25 |
| 4,215,409 | 7/1980 | Strowe | 128/203.14 |
| 4,266,573 | 5/1981 | Braatz | 128/203.25 |
| 4,328,823 | 5/1982 | Schreiber | 128/203.25 |
| 4,345,612 | 8/1982 | Koni et al. | 128/203.14 |
| 4,442,856 | 4/1984 | Betz | 128/203.14 |
| 4,549,563 | 10/1985 | Monnier | 128/203.14 |
| 4,832,014 | 5/1989 | Perkins | 128/203.12 |

FOREIGN PATENT DOCUMENTS

| | | | |
|---|---|---|---|
| 2041225 | 9/1980 | United Kingdom | 128/203.12 |
| 2133714 | 8/1984 | United Kingdom | 128/203.25 |
| 2136703 | 9/1984 | United Kingdom | 128/203.12 |

Primary Examiner—Edgar S. Burr
Assistant Examiner—Kimberly L. Asher
Attorney, Agent, or Firm—McGlew and Tuttle

[57] ABSTRACT

A gas ratio controlling device for anesthetic appliances, wherein the throughput ratio of oxygen to anesthetic gas (oxygen:anesthetic gas) is controlled by means of a control circuit with a control valve operating depending on the concentration parameters required. The oxygen ratio in the supply gas must not fall below a preset value. The control is improved in order to secure that the oxygen content does not fall below the required minimum during small gas mixture flow rates and the invention provides a means of adjustment for small anesthetic gas values. According to the invention this is achieved by a control valve situated in the anesthetic gas supply line which can be bridged by a by-pass line having a throttle.

3 Claims, 1 Drawing Sheet

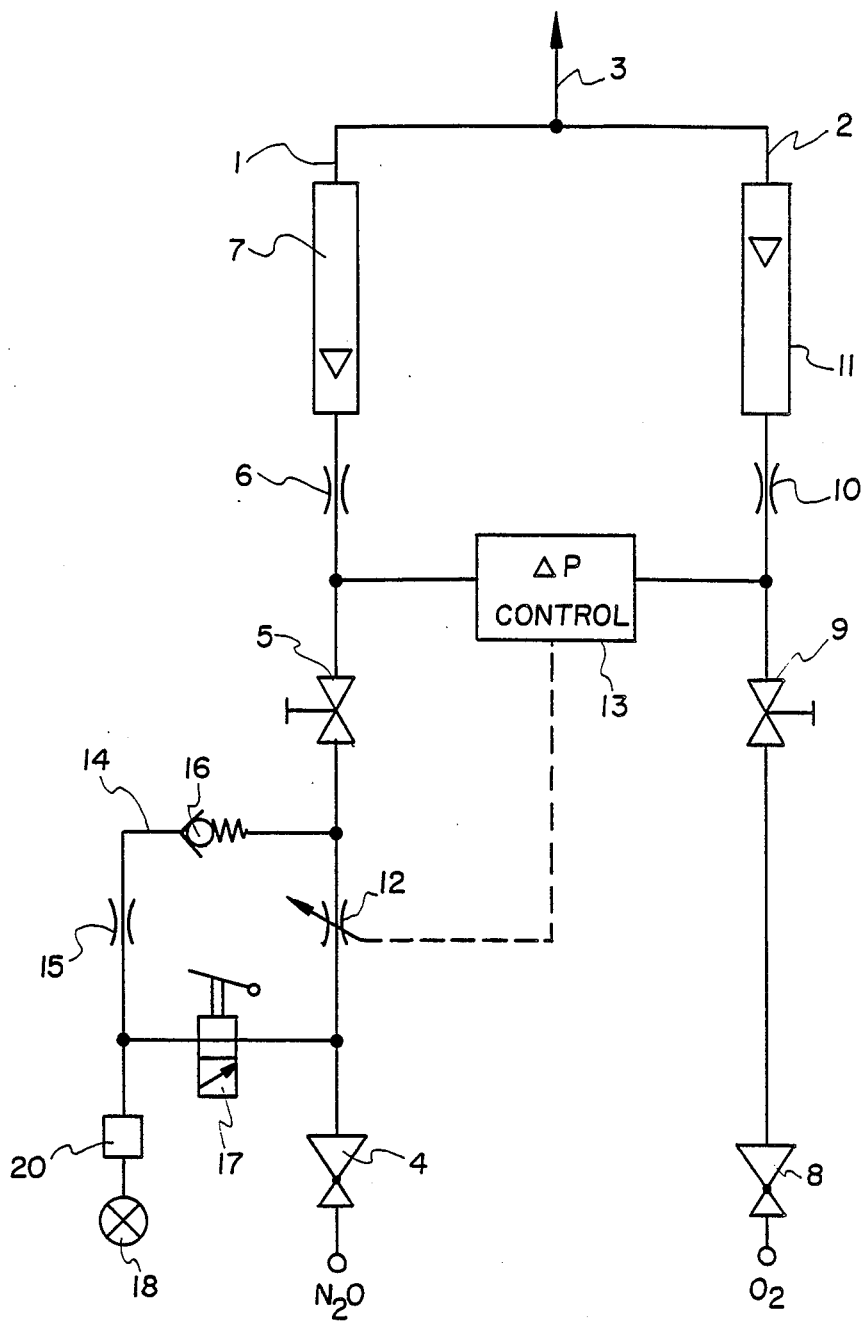

GAS RATIO CONTROLLING DEVICE FOR ANESTHETIC APPLIANCES

FIELD AND BACKGROUND OF THE INVENTION

This invention relates in general to anesthetic appliances and in particular to a new and useful device for accurately controlling the rate at which oxygen and anesthetic are fed to a patient.

A gas ratio controlling device for anesthetic appliances is disclosed, wherein the throughput ratio of oxygen to anesthetic gas is controlled by means of a control circuit via a control valve depending on the concentration parameters required, while the oxygen ratio in the supply gas must not fall below a preset value.

Anesthetic appliances are equipped with so-called "oxygen ratio controllers" to simplify usage and to reduce the chance of operator's errors. These controllers forcibly reduce the anaesthetic gas throughput when the oxygen concentration reaches a preset bottom value in a way that does not allow the oxygen concentration to fall below this preset oxygen concentration in the gas mixture.

According to German OS No. 33 10 858 such a gas ratio controlling device could be achieved e.g. by mechanically coupling the operating elements for the anaesthetic gas and oxygen adjustment valves so that the ratio of oxygen to anaesthetic gas is fixed independent of the chosen setting. The prior art gas ratio controlling device features also a by-pass line in the oxygen supply line, which can bridge the oxygen adjustment valve, so that the oxygen ratio in the gas mixture supplied to the patient can be increased independently of the coupling of the oxygen adjustment valve with the anaesthetic gas adjustment valve.

Another version of a gas ratio controlling device for anaesthetic appliances is described in the European PS No. 0 039 932. Herein the anesthetic gas is led into an anesthetic gas supply line comprising a pressure reducer and a proportional control valve, which is positioned upstream of the anesthetic gas adjustment valve. The dosed anesthetic gas flows to a common gas mixture outlet via a precision resistor and a flow meter tube for dosage indication purposes. The oxygen is led to this gas mixture outlet via an oxygen supply line, which also comprises a pressure reducer, an adjustment valve, a precision resistor and a flow meter. At the precision resistors the gas flows create dynamic pressures which are fed into a final control element which controls the proportional control valve according to the difference in the two dynamic pressure values so that the supply of anesthetic gas does not exceed a certain value with regard to its ratio to the oxygen supply. Thus it is guaranteed that the patients gas mixture supply contains at least a certain preset oxygen concentration, e.g. 25% by Vol.

Typical doses for such gas ratio controlling devices range from 3 liter/min to 30 liter/min gas mixture supply. Difficulties can arise when a small throughput is required as the correspondingly small dynamic pressures do not allow for a safe or accurate control of the proportional control valve.

Therefore appropriate means have to guarantee that below a smallest adjustment value for the oxygen throughput of, for example, one liter per minute the anesthetic gas supply is completely blocked by the proportional control valve, i.e. the oxygen concentration in the gas mixture rises to 100 Vol %.

Therefore, in forms of narcosis with very small gas mixture flow rate adjustment problems occur when, in certain phases of the anaesthesia, small doses of the gas are required, which should take into account the needs of the patient, losses through leakage plus a certain safety margin. In practice the total gas mixture amount is reduced to values down to 0.5 liter/min. These kinds of narcosis with very small gas mixture flow rates do not allow for the use of any of the prior art oxygen ratio controllers, as they can not be controlled with adequate safety.

While at a gas mixture flow rate of one liter per minute the flow rate of the anesthetics gas system alone of about 5 minutes is relatively long and there is therefore enough time for the recognition and the correction of maladjustments, the danger potential increases with higher gas mixture flow rates and can be tolerated no longer.

It is necessary that the gas ratio control devices described above are constructed in a way that guarantees a constant safe operation with adjustable, small amounts of anesthetic gas and with higher gas mixture flow rates.

SUMMARY OF THE INVENTION

According to the invention a control valve positioned in the anaesthetic gas line is connected to a by-pass comprising a throttle. By this means the anaesthetic gas can be dosed according to the requirements in medically relevant magnitudes even with small oxygen flow rates of one liter per minute or less, at which rates the control valve is completely closed. Even if an operator's error occurs, in respect to the throttle, several minutes will lapse before a state dangerous for the patient could occur. Also, such a state would be recognized in time due to the prescribed oxygen concentration control in the supplied mixed gas and can be eliminated without endangering the patient. The size of the throttle is therefore to be calibrated so that even with an operating mistake, i.e. with the oxygen adjustment valve closed, there will be enough time for the recognition of a state dangerous to the patient. Generally, a period of five minutes is sufficient.

Beyond a gas mixture flow rate of two liters per minute no restrictions for the safe operation of the gas ratio control device are necessary. The by-pass line is to be opened and closed preferably by means of a manually operated reversing valve. If anaethesia with minimal gas mixture flow rates is not required, the by-pass can be switched off by means of the reversing valve.

An additional advantage might be achieved by arranging a pressure switch in the by-pass line. The pressure switch controls a signalling element which emits a warning signal when the by-pass line is in operation. This signal may be of optical and/or acoustic nature. It indicates to the operator that the by-pass line of the anesthetics appliance is in operation and that therefore increased care has to be taken with regard to the surveillance of the oxygen supply at very small gas mixture flow rates.

In a further embodiment of the invention it may be advantageous to arrange a non-return valve in the by-pass line to the effect that the connection with the anesthetic gas supply line is interrupted when the by-pass is shut-off and the by-pass line is open to the atmosphere. This non-return valve avoids that anesthetic gas is expelled continuously while the line is vented via the switch valve to reset the signalling elements.

An advantageous embodiment of the gas ratio control device may be designed so that an anaesthetic gas supply line and an oxygen supply line both end in a gas mixture outlet. The anaesthetic gas supply line and the oxygen supply line are each equipped with a pressure reducer, a precision adjustment valve, a precision resistor for measurement purposes and a flow meter tube mounted in series. The differential pressure measured upstream of the precision resistors is fed into a differential pressure or control means controller.

The proportional action controller controls a control valve positioned in the anesthetic gas supply line between the pressure reducer and the precision adjustment valve. The control valve is bridged by means of a by-pass line containing the throttle the non-return valve and the switch valve. The switch valve cuts off the by-pass via the control valve in one of its switch positions.

Accordingly, it is an object of the invention to provide a gas ratio controlling device for anesthetic appliances so that the ratio of oxygen to anesthetic gas is controlled by means of a control circuit which has a control valve with sensing means in each of the oxygen and anesthetic lines and is connected to a control valve in the anesthetic gas line sc as to maintain an oxygen ratio which does not fall below a preset value and wherein the control valve is bridged by a by-pass line which has a separate throttle.

A further object of the invention is to provide a device for controlling the supply of oxygen and an anesthetic gas to a patient which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

BRIEF DESCRIPTION OF THE DRAWINGS

In the drawings:

The only FIGURE of the drawings is a schematic representation of an apparatus for supplying anesthesia to a patient constructed in accordance with the invention.

DESCRIPTION OF THE PREFERRED EMBODIMENT

Referring to the drawing in particular the invention embodied therein comprises a gas ratio controlling device for anesthetic appliances which includes an anesthetic supply line 1 and an oxygen supply line 2 which are fed into a gas mixture outlet 3 and supplied to a patient. In accordance with the invention, a differential action control element or control means 13 is connected to the anesthetic supply line 1 and to the oxygen supply line 2 and it acts to control a proportional control valve 12 to regulate the anesthetic supply so as to ensure the supply of oxygen (ensure a proper oxygen/anesthetic ratio). Control means act in dependence on the condition sensed in each of the supply lines. In accordance with the invention, a control valve 12 in the anesthetic line is arranged so that it is bridged by a by-pass line 14 which has a flow restrictor or throttle 15 which may be regulated to dose the anesthetic gas according to the requirements in medically relevant magnitudes even with small oxygen flow rates; for example during a time when the control valve is completely closed.

The anesthetic gas supply line 1 and the oxygen supply line 2 end together in the gas mixture outlet 3. The anaesthetic gas supply line is equipped with a pressure reducer 4, an anaesthetic gas precision adjustment valve 5, a precision resistor for measurement purposes 6, and a flow meter tube 7. The oxygen gas supply line 2 is also equipped with a pressure reducer 8, an anesthetic gas precision adjustment valve 9, a flow restrictor or precision resistor for measurement purposes 10 and a flow meter tube 11.

In the anesthetic gas supply line 1 the proportional control valve 12 is positioned between the pressure reducer 4 and the anaesthetic gas precision adjustment valve 5. The proportional control valve 12 is controlled by control means 13 reacting to the differential pressure ($\Delta P$) taken by the flow restrictors or precision resistors 6, 10.

The proportional control valve 12 in the anesthetic gas supply line 1 can be bridged by means of a by-pass line 14 containing a flow restrictor or throttle 15 and a spring-loaded non-return valve 16. The actuation of the by-pass line 14 for the bridging of the proportional control valve 12 is effected by a manually operated switch valve 17, which is shown open in the drawing, i.e. the by-pass is inactive. The by-pass line 14 is connected via a pressure switch 20 to an optical signaling element or indicator 18, which indicates the switch position of the switch valve 17, in particular the operation of the by-pass.

While a specific embodiment of the invention has been shown and described in detail to illustrate the application of the principles of the invention, it will be understood that the invention may be embodied otherwise without departing from such principles.

What is claimed is:

1. A gas ratio controlling device for anesthetic appliances, comprising an oxygen supply line, an anesthetic gas supply line connected to said oxygen supply line, a gas mixture outlet connected at the juncture of said oxygen supply line and said anesthetic gas supply line, a control valve in said anesthetic gas supply line for regulating the flow of anesthetic gas therethrough, control means for said control valve connected thereto and having a connection in each of said anesthetic gas supply line and said oxygen supply line and acting in accordance with differences in pressure in said anesthetic supply line and said oxygen supply line to maintain a predetermined pressure ratio between oxygen and anesthetic to ensure that anesthetic gas does not exceed a selected ratio to the oxygen, and a by-pass line connected around said control valve, and a throttle in said by-pass line for controlling the amount of anesthetic gas passing therethrough, a non-return valve in said by-pass line between said throttle and said anesthetic gas supply line for shutting off the anesthetic gas supply when said by-pass line is cut off, and including means for venting said by-pass line.

2. A gas ratio controlling device for anesthetic appliances, comprising an oxygen supply line, an anesthetic gas supply line connected to said oxygen supply line, a gas mixture outlet connected at the juncture of said oxygen supply line and said anesthetic gas supply line, a control valve in said anesthetic gas supply line for regulating the flow of anesthetic gas therethrough, control means for said control valve connected thereto and having a connection in each of said anesthetic gas supply line and said oxygen supply line and acting in accordance with differences in pressure in said anesthetic supply line and said oxygen supply line to maintain a predetermined pressure ratio between oxygen and anesthetic to ensure that anesthetic gas does not exceed a selected ratio to the oxygen, and a by-pass line connected around said control valve, and a throttle in said by-pass line for controlling the amount of anesthetic gas passing therethrough, said anesthetic gas line and said oxygen supply line includes a pressure reducer, a precision adjustment valve, a precision resistor for measurement purposes and a flowmeter tube all mounted in a series, said precision resistor providing means for obtaining a differential pressure measurement which is fed to said control means, said control valve being arranged in said anesthetic gas supply line between said pressure reducer and said pressure adjustment valve, said by-pass line including a throttle, a non-return valve, and a switch valve, said switch valve cutting off the by-pass around said control valve in one of its switch positions.

3. A gas ratio controlling device according to claim 1, wherein said non-return valve comprises a spring loaded valve.

* * * * *